(12) United States Patent
Ogura et al.

(10) Patent No.: US 9,251,995 B2
(45) Date of Patent: Feb. 2, 2016

(54) RADIATION GENERATING TUBE AND RADIATION IMAGING APPARATUS USING THE SAME

(75) Inventors: Takao Ogura, Yokohama (JP); Kazuyuki Ueda, Tokyo (JP); Yasue Sato, Machida (JP); Ichiro Nomura, Atsugi (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 92 days.

(21) Appl. No.: 14/127,647

(22) PCT Filed: Jul. 17, 2012

(86) PCT No.: PCT/JP2012/068543
§ 371 (c)(1),
(2), (4) Date: Dec. 19, 2013

(87) PCT Pub. No.: WO2013/031423
PCT Pub. Date: Mar. 7, 2013

(65) Prior Publication Data
US 2014/0140480 A1 May 22, 2014

(30) Foreign Application Priority Data

Aug. 31, 2011 (JP) ................. 2011-189108

(51) Int. Cl.
*H01J 35/00* (2006.01)
*H01J 35/16* (2006.01)
(Continued)

(52) U.S. Cl.
CPC .............. *H01J 35/165* (2013.01); *G01N 23/04* (2013.01); *H01J 35/08* (2013.01); *H01J 35/16* (2013.01); *H01J 35/18* (2013.01); *H01J 2235/087* (2013.01); *H01J 2235/166* (2013.01); *H01J 2235/186* (2013.01)

(58) Field of Classification Search
CPC ......... H01J 35/165; H01J 35/16; H01J 35/08; H01J 35/18; H01J 2235/087; H01J 2235/166; H01J 2235/186; G01N 23/04
USPC .................................. 378/119, 121, 122, 140
See application file for complete search history.

(56) References Cited

U.S. PATENT DOCUMENTS 6,044,130 A * 3/2000 Inazura et al. ................. 378/138
6,487,272 B1 11/2002 Kutsuzawa .................... 378/140
(Continued)

FOREIGN PATENT DOCUMENTS

JP   2000-306533 A   11/2000
JP   2002-298772 A   10/2002
(Continued)

*Primary Examiner* — Courtney Thomas
(74) *Attorney, Agent, or Firm* — Fitzpatrick, Cella, Harper & Scinto

(57) ABSTRACT

A radiation generating tube 1 includes: an electron emitting source 3; a target 9 spaced from the electron emitting source 3, for generating radiation 11 responsive to irradiation with an electron beam from the electron emitting source 3; and a tubular shielding member 10 having an electron passing hole 8, wherein the electron passing hole 8 has an electron incident aperture at one end thereof and has a target supporting surface 9b supporting the target 9 at the other end thereof, wherein the target supporting surface 9b is connected through a brazing filler 14 to a periphery of a surface of the target at a side on which the electron is incident, and an opening size of the other end of the electron passing hole 8 is larger than an opening size of the electron incident aperture at the one end thereof.

22 Claims, 3 Drawing Sheets

(51) Int. Cl.
*H01J 35/08* (2006.01)
*H01J 35/18* (2006.01)
*G01N 23/04* (2006.01)

(56) References Cited

U.S. PATENT DOCUMENTS

| | | | |
|---|---|---|---|
| 6,572,426 B1 | 6/2003 | Inazuru | 445/28 |
| 6,850,598 B1 | 2/2005 | Fryda et al. | 378/161 |
| 7,991,120 B2 | 8/2011 | Okunuki et al. | 378/124 |
| 8,472,585 B2 | 6/2013 | Ogura et al. | 378/111 |
| 2002/0085674 A1 | 7/2002 | Price et al. | 378/122 |
| 2006/0280290 A1 | 12/2006 | Matsumura et al. | 378/140 |
| 2012/0140895 A1 | 6/2012 | Okunuki et al. | 378/122 |
| 2012/0307974 A1 | 12/2012 | Yamazaki et al. | 378/62 |
| 2012/0307978 A1 | 12/2012 | Yamazaki et al. | 378/121 |
| 2013/0016810 A1 | 1/2013 | Tamura et al. | 378/62 |
| 2013/0016811 A1 | 1/2013 | Ueda et al. | 378/62 |
| 2013/0016812 A1 | 1/2013 | Yanagisawa et al. | 378/62 |
| 2013/0230143 A1 | 9/2013 | Ueda et al. | 378/62 |
| 2013/0235975 A1 | 9/2013 | Tamura et al. | 378/62 |
| 2014/0140486 A1 | 5/2014 | Yanagisawa et al. | 378/141 |
| 2014/0153695 A1 | 6/2014 | Yanagisawa et al. | 378/142 |
| 2014/0177800 A1 | 6/2014 | Sato et al. | 378/121 |

FOREIGN PATENT DOCUMENTS

| | | |
|---|---|---|
| JP | 2002-352755 | 12/2002 |
| JP | 2003-505845 | 2/2003 |
| JP | 2007-265981 A | 10/2007 |
| JP | 2008-135397 | 6/2008 |
| WO | WO 03/065772 A2 | 7/2003 |
| WO | 2008/156361 | 12/2008 |

* cited by examiner

FIG. 1A
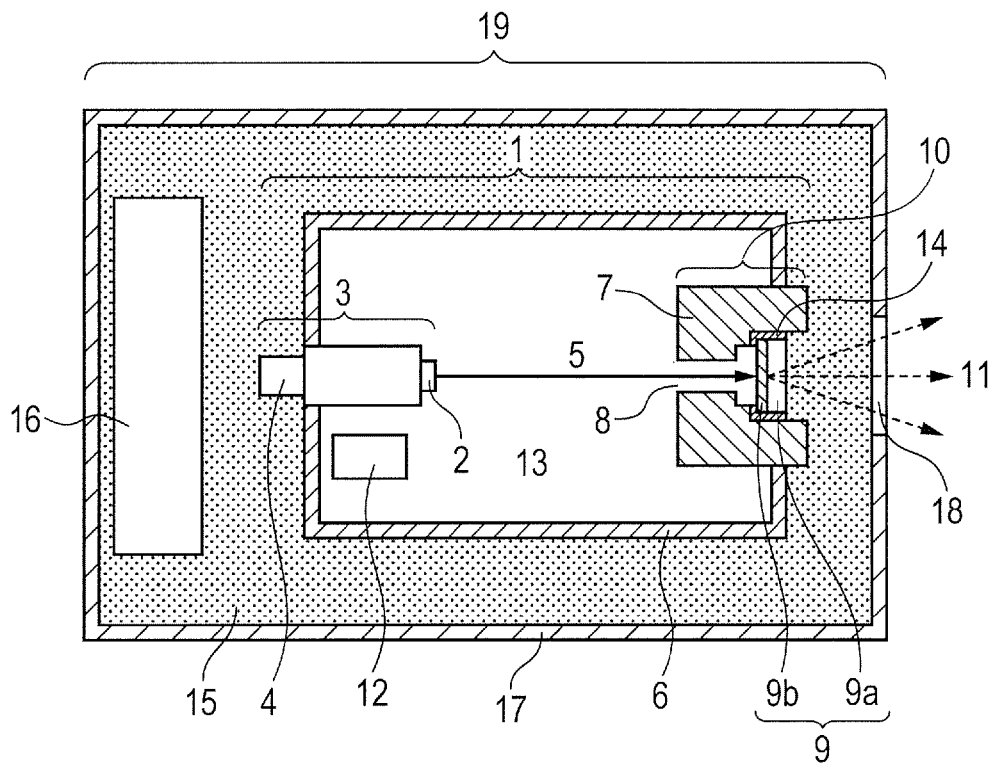
FIG. 1B
FIG. 1C
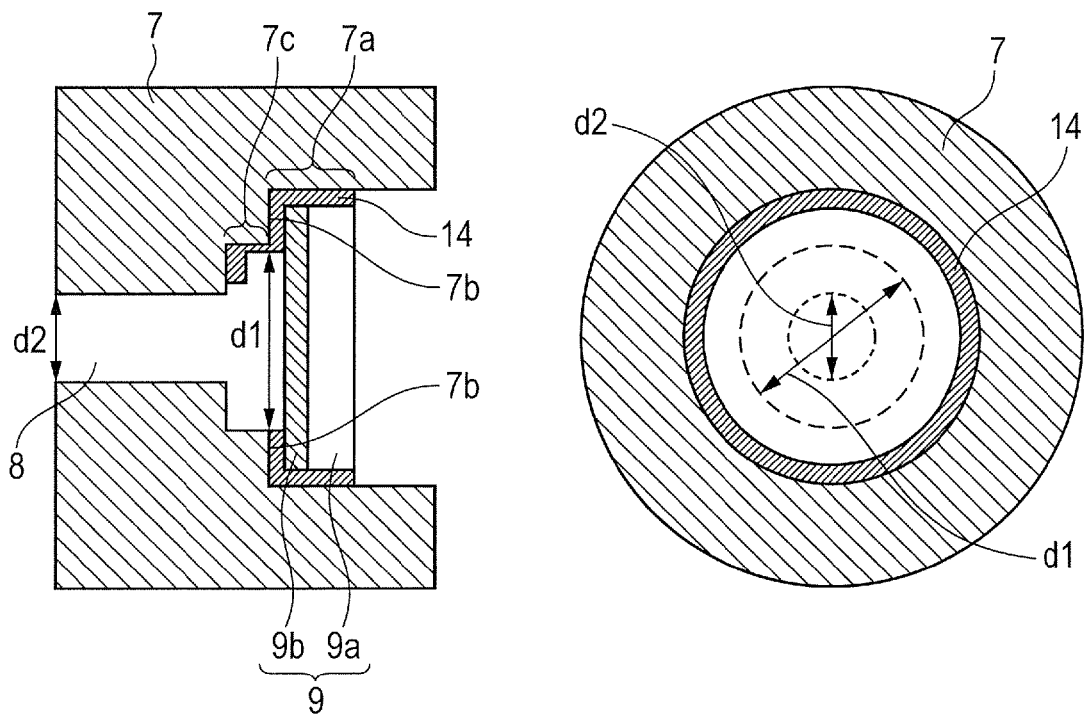

RADIATION GENERATING TUBE AND RADIATION IMAGING APPARATUS USING THE SAME

TECHNICAL FIELD

The present invention relates to a radiation generating tube which generates radiation by irradiating a target with electrons, and can be applied to X-ray photography and the like, and to a radiation imaging apparatus using the same.

BACKGROUND ART

A radiation generating tube, which is used as a radiation source, generates radiation by emitting electrons from an electron source within the radiation generating tube (radiation emitting source) in which a vacuum is maintained, and making the electrons collide with the target, which is formed from a metal material such as tungsten having a large atomic number.

Incidentally, in order to efficiently generate electrons from an electron source and to extend the life of the radiation generating tube, it is necessary to keep the inside of the radiation generating tube at a vacuum for a long period of time. Japanese Patent Application Laid-Open No. 2000-306533 discloses a technique for keeping the inside of the radiation generating tube at a vacuum by brazing the perimeter of the target to a target holding ring of the radiation generating tube (X-ray tube), in a radiation generating tube that uses a transmitting type target.

In addition, in the radiation generating tube, the radiation generated in the target is emitted in all directions, and accordingly, it is general to shield the unwanted radiation, that is, radiation other than that required for photography, by providing a radiation shielding member. Japanese Patent Application Laid-Open No. 2007-265981 discloses a structure in which the radiation shielding member is arranged at the electron incident side and the radiation extraction side of the transmitting type target.

CITATION LIST

Patent Literature

1: Japanese Patent Application Laid-Open No. 2000-306533
2: Japanese Patent Application Laid-Open No. 2007-265981

SUMMARY OF INVENTION

Technical Problem

A known method for keeping the vacuum inside the radiation generating tube and shielding the unwanted radiation is to shield the radiation which diffuses in an unwanted direction by forming an electron passing hole and a radiation passing hole with the radiation shielding member in the perimeter of the target. Furthermore, a structure is known in which the connection of the shielding member to the target has airtightness by brazing the target to the radiation shielding member.

However, when the target is bonded to the radiation shielding member with a brazing technique for the purpose of vacuum sealing, excess brazing filler flows out and occasionally flows even onto the inner surface of the electron passing hole provided in the radiation shielding member. The amount of the brazing filler used is determined in advance, and is based on the size of the gap between the radiation shielding member and the target, but if the parts have a certain dimensional tolerance, excess brazing filler flows out. If the brazing filler has flowed onto the inner surface of the electron passing hole, an electron beam may directly irradiate the brazing filler. The brazing filler has a lower melting point than the target and the peripheral radiation shielding member, and accordingly is melted when impinged on by the electron beam, and the quality of the vacuum inside the radiation generating tube is reduced as a result. In addition, when the degree of vacuum inside the radiation generating tube is lowered, it becomes more difficult to generate thermal electrons from the electron source, and the quantity of radiation which can be extracted decreases. Thus, a problem is that the radiation generating tube consequently cannot be used continuously for as long as might be desirable.

For this reason, an object of the present invention is to provide a radiation generating tube which has such a structure that brazing filler is not directly irradiated by the electron beam, thereby suppressing degradation of the vacuum inside the radiation generating tube, which can generate a stable quantity of radiation as a result, and can be continuously used for a long period of time, and to provide a radiation imaging apparatus using the same.

Solution to Problem

According to an aspect of the present invention, a radiation generating tube comprises: an electron emitting source; a target spaced from the electron emitting source, for generating radiation responsive to irradiation with an electron emitted from the electron source; and a tubular shielding member having an electron passing hole, where the electron passing hole has an electron incident aperture at one end thereof and has a target supporting surface supporting the target at the other end thereof, and where the target supporting surface is connected by a brazing filler to a periphery of a surface of the target at a side on which the electron is incident, and an opening size of the other end of the electron passing hole is larger than an opening size of the electron incident aperture at the one end thereof.

According to a further aspect of the present invention, a radiation generating tube comprises: an electron emitting source; a target spaced from the electron emitting source, for generating radiation responsive to irradiation with an electron emitted from the electron source; and a tubular shielding member having an electron passing hole, where the electron passing hole has an electron incident aperture at one end thereof and has a target supporting surface supporting the target at the other end thereof, with the target supporting surface connected by a brazing filler to a periphery of a surface of the target at a side on which the electron is incident, and the tubular shielding member has an annular recess which is arranged along the target supporting surface, and is recessed in a direction of increasing a distance from the target supporting surface.

Advantageous Effects of Invention

The radiation generating tube according to the present invention has such a structure that even if brazing filler has flowed onto and forms a deposit on the inner surface of an electron passing hole provided in a radiation shielding member, the brazing filler which has flowed out is not directly irradiated with the electron beam. Thereby, the brazing filler which has flowed out is not melted by being directly irradiated with the electron beam, and accordingly the radiation generating tube can avoid the conventional degradation of the vacuum in its interior, and can avoid the lowering of the quantity of radiation that the tube is able to output when having been continuously used for a long period of time.

Further features of the present invention will become apparent from the following description of exemplary embodiments with reference to the attached drawings.

BRIEF DESCRIPTION OF DRAWINGS

FIGS. 1A, 1B and 1C are diagrams partly in section of a radiation generating tube of the present invention, and views illustrating an example of an anode.

DESCRIPTION OF EMBODIMENTS

Figure 2A:
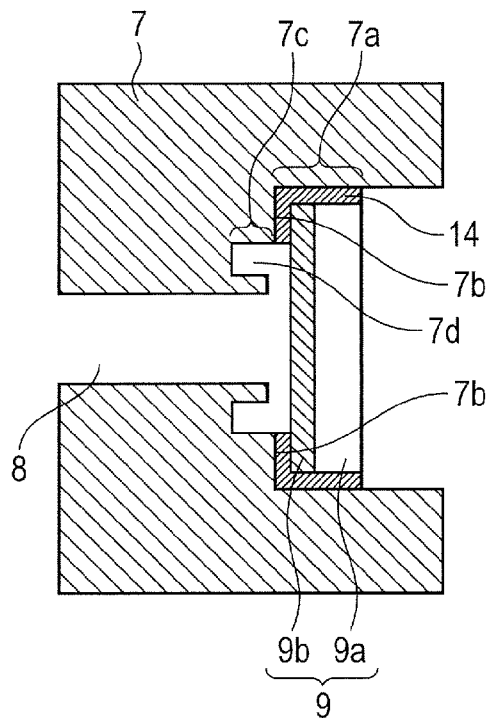
FIGS. 2A, 2B, 2C and 2D are views illustrating other examples of an anode used for the radiation generating tube of the present invention.

Embodiments suitable for a radiation generating tube according to the present invention will be illustratively described in detail below with reference to the drawings. However, the materials, dimensions, shapes, relative arrangements and the like of the components which are described in the following embodiments do not limit the scope of the present invention only to those shown and described, unless otherwise specified.

First Embodiment

A structure of a radiation generating tube of a first embodiment will be described below with reference to FIGS. 1A to 1C. FIG. 1A is a sectional view illustrating an example of structure of the radiation generating tube of the present embodiment; FIG. 1B is a sectional view enlargingly illustrating the anode of FIG. 1A; and FIG. 1C is a plan view of the anode of FIG. 1A when viewed from the radiation extraction window side.

The radiation generating tube 19 is structured so as to have a radiation emitting source 1 and a driving power source 16 arranged in an envelope 17 having the radiation extraction window 18, and so as to have a space left in the envelope 17 filled with an insulating oil 15.

The radiation emitting source 1 includes an electron emitting source 3, the anode 10, a getter 12 and a vacuum chamber 6.

The electron emitting source 3 includes an electric-current introduction terminal 4 and an electron emitting portion 2. An electron emission mechanism of the electron emitting source 3 may be an electron emitting source which can control the amount of electrons to be emitted from the outside of the vacuum chamber 6, and a hot cathode electron emitting source, a cold cathode electron emitting source and the like can be appropriately applied to the electron emission mechanism. The electron emitting source 3 is electrically connected to the driving power source 16 arranged in the outside of the vacuum chamber 6 so that the amount of electrons to be emitted and an ON/OFF state of the electron emission can be controlled through the electric-current introduction terminal 4 which is arranged so as to penetrate the vacuum chamber 6.

The electrons which have been emitted from the electron emitting portion 2 are converted into an electron beam 5 having an energy of approximately 10 keV to 200 keV by a drawing grid (not shown) and an accelerating electrode (not shown), and is incident on a target 9 which is arranged to oppose the electron emitting portion 2. The drawing grid and the accelerating electrode can also be housed in an electron gun tube of the hot cathode. Alternately, it is also possible to add a correcting electrode for adjusting the position of the spot to be irradiated with the electron beam and the astigmatism of the electron beam, to the electron emitting source 3, and then to connect the electron emitting source 3 to a correcting circuit (not shown) which is arranged in the outside.

The anode 10 includes a radiation shielding member 7 and a target 9 including a target substrate 9a and a target film 9b.

Typically, a metal material having an atomic number of 24 or more can be used for the target film 9b. The metal material can be used which has larger thermal conductivity and a higher melting point. Specifically, the usable metal materials can be a metal material such as tungsten, molybdenum, chromium, copper, cobalt, iron, rhodium and rhenium, or an alloy material thereof. The value of the thickness of the target film 9b is 1 µm to 15 µm, although the optimal value varies depending on an accelerating voltage, because an infiltration depth of the electron beam into the target film 9b (in other words, a region in which the radiation is generated) varies depending on the accelerating voltage. The above-described thickness of the target film 9b can be specified as a thickness in a normal direction with respect to the surface of the target substrate 9a in a side having the target film 9b provided thereon.

The target film 9b can be integrated with the target substrate 9a by sputtering, vapor deposition or the like. As another method, the target film 9b can be integrated with the target substrate 9a by separately preparing a thin film of the target film 9b having a predetermined thickness with a rolling or polishing process, and diffusion-bonding the target film 9b to the target substrate 9a under a high temperature and a high pressure.

A covering form of the target film 9b for the target substrate 9a of the present invention is not limited to a form (coverage of 100%) in which the target film 9b covers the entire one main surface, as in FIG. 1B. The target film 9b of the present invention includes a form in which the target film 9b is only partially formed on the target substrate 9a, in consideration of an electron irradiation range in which the target 9 is irradiated with electrons. The present invention includes, for instance, a form in which the target film 9b covers 10% to 90% by an area ratio with respect to the area of the surface of the target substrate 9a in a side opposing to the electron emitting source 3. In a form in which the target film does not extend peripheral portion of the target substrate not to cover the whole target substrate, the form is enabled to have an electrode (not shown) formed in a space between an area in which the target film is formed and the peripheral portion of the target substrate, for the purpose of specifying an anode potential of the target film. In addition, in this target having such a partially covered form, a target supporting surface can be any of a form supporting the target by supporting only the peripheral portion of the target substrate, or supporting the target by supporting the peripheral portion of the target substrate and the peripheral portion of the target film.

The target substrate 9a needs to have high transmissivity for radiation and adequate thermal conduction and withstand vacuum sealing. For instance, diamond, silicon nitride, silicon carbide, aluminum carbide, aluminum nitride, graphite, beryllium or the like can be used for the target substrate 9a. The target substrate 9a can more desirably contain any one of the diamond, the aluminum nitride and the silicon nitride which have smaller transmissivity for radiation than that of the aluminum and larger thermal conduction than that of the tungsten, as a main ingredient. The thickness of the target substrate 9a may satisfy the above described functions, and can be 0.3 mm or more and 2 mm or less, though varying depending on the material. Particularly, the diamond is more excellent because of having extremely higher thermal conductivity than that of other materials, having also high transmissivity for radiation and being easy to keep the vacuum. However, in these materials the thermal conductivity falls considerably as the temperature rises, and accordingly the target substrate 9a needs to suppress the rise of temperature as much as possible. The above-described thickness of the target substrate 9a can be specified as a thickness in the normal direction with respect to the coated surface of the target substrate 9a in a side having the target film 9b provided thereon.

The radiation shielding member 7 has the electron passing hole 8 having an opening formed in each of both ends. Electrons are incident from one end (opening in end of electron emitting source 3 side) of the electron passing hole 8, and irradiate the target 9 provided in the other end side (opposite side of electron emitting source 3) of the electron passing hole 8 to generate the radiation. The electron passing hole 8 serves as a passage for guiding the electron beam 5 therethrough into an electron beam irradiation region (radiation generating region) of the target film 9b, in a side closer to the electron emitting source 3 than the target 9, and serves as a passage for emitting the radiation therethrough to the outside, at the side closer to the radiation extraction window 18 than the target 9. Unwanted radiation such as radiation be emitted generally toward the electron emitting source 3 from the target film 9b and radiation emitted other than in the desired path to the radiation extraction window 18 is shielded by the inner wall of the electron passing hole 8. The electron passing hole 8 has a circular shape in a plan view as seen from the radiation extraction window 18 side, as is illustrated in FIG. 1C, but can instead have a quadrangle, an ellipse shape or the like. In addition, the radiation shielding member 7 contacts the insulating oil 15, and accordingly has also a function of transmitting a heat generated in the target 9 to the insulating oil, and dissipating the heat to the outside of the radiation emitting source 1.

The material which can be used for the radiation shielding member 7 may be a material which can shield a radiation generated at 30 kV to 150 kV. The usable materials are, for instance, molybdenum, zirconium, niobium or the like in addition to tungsten and tantalum, or an alloy material thereof.

The radiation shielding member 7 and the target 9 can be bonded to each other with a brazing technique or the like. When the member and the target are bonded with the brazing technique, it is important to keep the inside of the vacuum chamber 6 at a vacuum state. A brazing filler for brazing can be appropriately selected according to the material, heat-resistant temperature and the like of the radiation shielding member 7. When the temperature of the target substrate 9a becomes especially high, for instance, a brazing filler metal such as a Cr—V series brazing material, a Ti—Ta—Mo series brazing material, a Ti—V—Cr—Al series brazing material, a Ti—Cr series brazing material, a Ti—Zr—Be series brazing material and a Zr—Nb—Be series brazing material can be selected as a brazing filler of a high-melting-point metal. When vacuum airtightness is regarded as more important, brazing materials such as an Au—Cu series brazing material, a nickel series brazing material, a brass series brazing material, a silver series brazing material, a palladium series brazing material and the like can be used as a brazing filler for high vacuum equipment.

The vacuum chamber 6 can be formed from glass, ceramics or the like, and the inside of the vacuum chamber 6 becomes an internal space 13 which has been evacuated (decompressed). The internal space 13 may have such a vacuum degree that electrons can fly at least a distance between the electron emitting source 3 and the target film 9b which emits the radiation, as a mean free path of the electrons, and a vacuum in which the pressure is $1 \times 10^{-4}$ Pa or less can be provided in the internal space. It is possible to appropriately select the vacuum degree in consideration of the electron emitting source to be used, the operating temperature and the like. In the case of a cold cathode electron emitting source, the pressure in the vacuum can further be set at $1 \times 10^{-6}$ Pa or less. In order to keep the vacuum quality, it is also possible to arrange the getter 12 in the internal space 13 as mentioned, or to place the getter 12 in a not-shown auxiliary space which communicates with the internal space 13.

The structure of the anode 10 will be described in detail below with reference to FIG. 1B. The anode 10 includes the radiation shielding member 7 having the electron passing hole 8 therein, the target substrate 9a which also serves as a radiation transmission window, and the target film 9b which is arranged on the surface in the electron emitting source 3 side of the target substrate 9a. The target supporting portion 7a having the target supporting surface 7b is provided in the radiation shielding member 7 in the perimeter in the other end side (perimeter in opposite side of end in electron incident side) of the electron passing hole 8. The periphery of the face at the side of the target 9 to be irradiated with electrons is brazed to the target supporting surface 7b, and the inside of the vacuum chamber 6 is kept at a vacuum. In addition, the radiation generating tube of the present invention adopts a structure in which the width d1 of a sectional area in the opening at the inner end (nearer the target 9) on the electron incident side of the electron passing hole 8 is larger than the width d2 of a sectional area at the outer end, where the electrons enter the electron passing hole 8, in other words, d1 is larger than an opening size d2 of an electron incident aperture. FIG. 1B illustrates a structure in which a brazing filler receiving portion 7c formed of one step shape from the target supporting surface 7b toward the end in the electron incident side of the electron passing hole 8, in other words, the electron incident aperture, is provided as an example. The electron passing hole 8 has a sectional area (inner diameter of electron passing hole 8) the width of which decreases step by step from the target supporting surface 7b toward the electron incident aperture at the left of FIG. 1B.

When the target 9 is brazed to the radiation shielding member 7, a metallization layer (not shown) is provided in advance in the perimeter of the target 9. As for the metallization layer, a paste is prepared, for instance, by adding a resinous bonding material and a dispersion medium to a metallization composition powder which contains a compound containing at least one element selected from Ti, Zr or Hf as an active metal component. After that, the metallization layer is obtained by applying the paste onto a portion to be metallized, and baking the applied paste at a predetermined temperature.

Next, an active brazing filler metal is deposited onto the metallized surface in the perimeter of the target 9. For instance, a Ti-containing silver-copper brazing filler can be used. The target 9 onto which this active brazing filler metal has been deposited is set in the target supporting portion 7a which is provided in the radiation shielding member 7 that has been formed to have a predetermined dimension, and is baked at a predetermined temperature for a predetermined period of time. These baking conditions vary depending on the type of the active brazing filler metal. The above described Ti-containing silver-copper brazing filler can be held at approximately 850° C. for approximately 100 seconds.

When the target 9 is bonded to the radiation shielding member 7 with a brazing technique, the inside of the vacuum chamber 6 needs to be kept vacuum-airtight, and accordingly this brazing is extremely important. Because of this, it is ideal that the brazing filler melts when it has been baked, and the target 9 and the radiation shielding member 7 can adhere to each other without forming a gap therebetween. However, certain variations result in occurring in the actual target 9, in the radiation shielding member 7, and even in the thicknesses of the metallization layer and the brazing filler, and accordingly a larger amount than an assumed average value of the brazing filler needs to be provided in the perimeter of the target 9, in order to keep at least the vacuum airtightness. Because of this, the brazing filler occasionally flows out along the inner surface of the electron passing hole 8 which has been provided in the radiation shielding member 7, when the brazing filler has been baked.

In the present embodiment, the width d1 of a sectional area in the opening in the opposite side of the end in the electron incident side of the electron passing hole 8 is made larger than the width d2 of the sectional area at the end at the electron incident side of the electron passing hole 8, in other words, an opening size d2 of an electron incident aperture. It is general to set the diameter of the electron beam to be smaller than d2. Because of this, even when the brazing filler flows from the target supporting surface 7b and is deposited on the inner surface of the electron passing hole 8, the radiation generating tube can prevent the electron beam from directly colliding with the deposited brazing filler.

In the structure of FIG. 1B, the mentioned one step shape is provided between the target supporting surface 7b and the electron-incident end of the electron passing hole 8, in other words so that d1 is larger than d2. Because of this, even if the brazing filler has flowed from the target supporting surface 7b and has reached the step shape, the brazing filler remains in the step shape, which can prevent the brazing filler from flowing down into the inner surface of the electron passing hole 8 closer to the electron incident side. Accordingly, the radiation generating tube having this construction can prevent the electron beam from directly colliding with the brazing filler, and even when the electron beam 5 irradiates the target in order to generate a radiation 11 there, the vacuum degree is little lowered.

Figure 3:
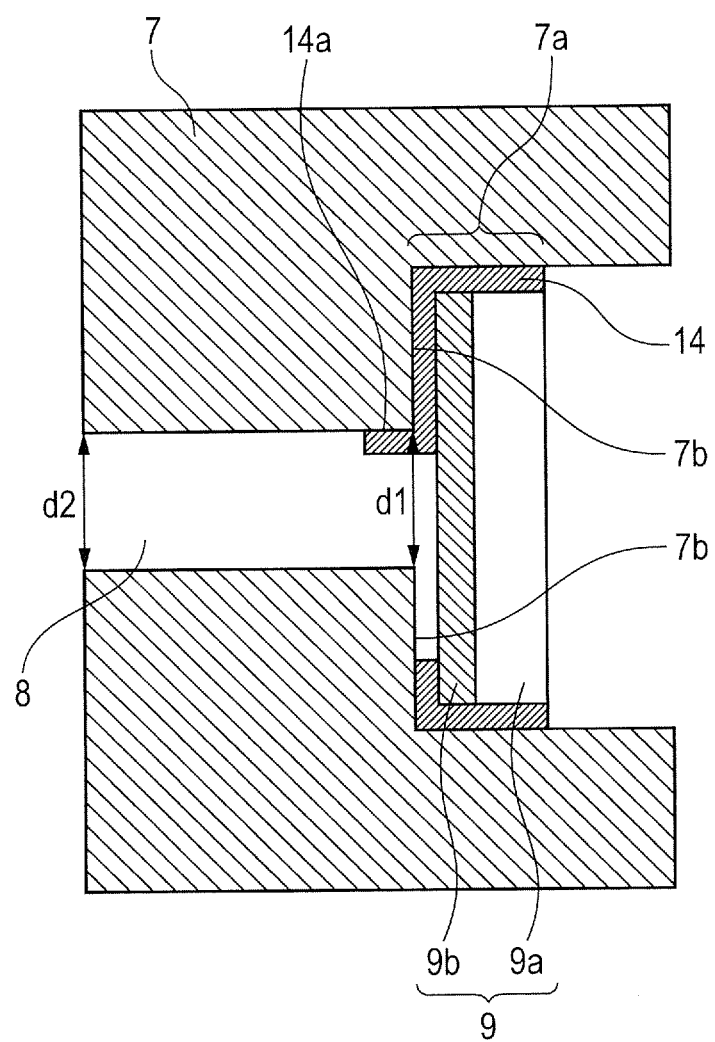
FIG. 3 is a view illustrating an anode of a comparative example.

On the other hand, as is illustrated in FIG. 3, when the width d1 of a sectional area in the opening in the opposite side of the end in the electron incident side of the electron passing hole 8 is the same as a width d2 of a sectional area in the end in the electron incident side of the electron passing hole 8, in other words, an opening size d2 of an electron incident aperture, if the brazing filler flows out, the brazing filler results in reaching the inner surface of the electron passing hole 8. When some portion of the brazing filler 14a is deposited on the inner surface of the electron passing hole 8, the brazing filler 14a that has flowed out is directly irradiated with the electron beam, which is different from the case of FIG. 1B. The brazing filler has a lower melting point than that of the target, and accordingly when the electron beam collides with the brazing filler, the metal 14a melts and tends to easily generate vapor. Because of this, the vacuum degree is lowered, the emission of electrons from the electron source decreases, and the quantity of radiation to be generated is reduced.

Thus, with the radiation generating tube according to the present embodiment, the anode 10 configured as shown in FIG. 1B can suppress the lowering of the vacuum degree and the lowering of the radiation quantity originating in the lowering of the vacuum degree.

Second Embodiment

A second embodiment will be described below with reference to FIG. 2A. FIG. 2A is a cross-sectional view enlargingly illustrating an anode in a radiation generating tube of the present embodiment.

The radiation generating tube of the present embodiment is provided with an annular recess 7d which is formed along the target supporting surface 7b and is recessed in a direction from the target supporting surface 7b toward the above-described electron incident aperture, that is in a direction of increasing a distance from the target supporting surface 7b, or decreasing a distance from the electron incident aperture, which is a point different from that in the first embodiment. Except for this point, the radiation generating tube of the present embodiment employs the same members as those in the first embodiment, and has the same structure as in the first embodiment.

In the structure of FIG. 2A, the anode is provided with an annular recess 7d which is formed along the target supporting surface 7b and is recessed in a direction from the target supporting surface 7b toward the above described electron incident aperture. The recess 7d constitutes a brazing filler receiving portion 7c, and the cross-sectional shape of the recess 7d becomes a rectangular shape. Because of this, even if the brazing filler has flowed from the target supporting surface 7b, the brazing filler remains in the recess 7d, and accordingly the radiation generating tube can prevent the brazing filler from flowing down to the inner surface of the electron passing hole 8. Therefore, the structure can prevent the electron beam from directly colliding with the brazing filler. In addition, in the structure of FIG. 2A, a surface distance can preferably be extended from the target supporting surface 7b to the inner surface of the electron passing hole 8 by providing the recess 7d. In the present disclosure, the phrase "surface distance from A to B is long" means that "the path is longer than a distance of connecting two points A and B with a straight line, in the cross section containing the two points A and B".

Thus, with the radiation generating tube according to the present embodiment, the anode 10 configured as shown in FIG. 2A can suppress the lowering of the vacuum degree and the lowering of the radiation quantity originating in the lowering of the vacuum degree, similarly to that in the first embodiment.

Third Embodiment

Figure 2B:
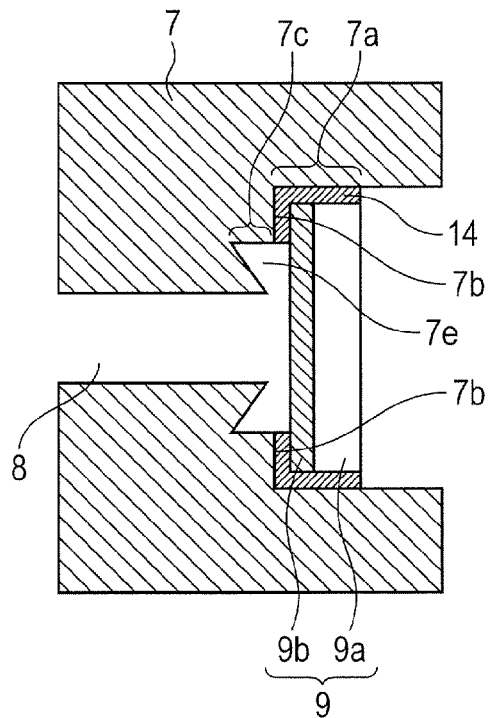

A third embodiment will be described below with reference to FIG. 2B. FIG. 2B is a cross-sectional view enlargingly illustrating an anode of a radiation generating tube of the present embodiment.

The radiation generating tube of the present embodiment is provided with an annular recess 7e that is formed along a target supporting surface 7b and is recessed in a direction from the target supporting surface 7b toward the above describe electron incident aperture, which is a point different from that in the first embodiment. Except for this point, the radiation generating tube of the present embodiment employs the same members as those in the first embodiment, and has the same structure as in the first embodiment.

In the structure of FIG. 2B, the radiation generating tube is provided with the annular recess 7e which is formed along the target supporting surface 7b and is recessed in the direction from the target supporting surface 7b toward the above described electron incident aperture. The recess 7e constitutes a brazing filler receiving portion 7c, and the cross-sectional shape of the recess 7e becomes a shape having an inclined slope. Because of this, even if the brazing filler has flowed from the target supporting surface 7b, the brazing filler remains in the recess 7e, and accordingly can prevent the brazing filler from flowing down to the inner surface of the electron passing hole 8. Therefore, the structure can prevent the electron beam from directly colliding with the brazing filler. In addition, in the structure of FIG. 2B, a distance can preferably be longer to the inner surface of the electron passing hole 8 by providing the recess 7e.

Thus, with the radiation generating tube according to the present embodiment, the anode 10 configured as shown in FIG. 2B can suppress the lowering of the vacuum degree and the lowering of the radiation quantity originating in the lowering of the vacuum degree, similarly to that in the first embodiment.

Fourth Embodiment

Figure 2C:
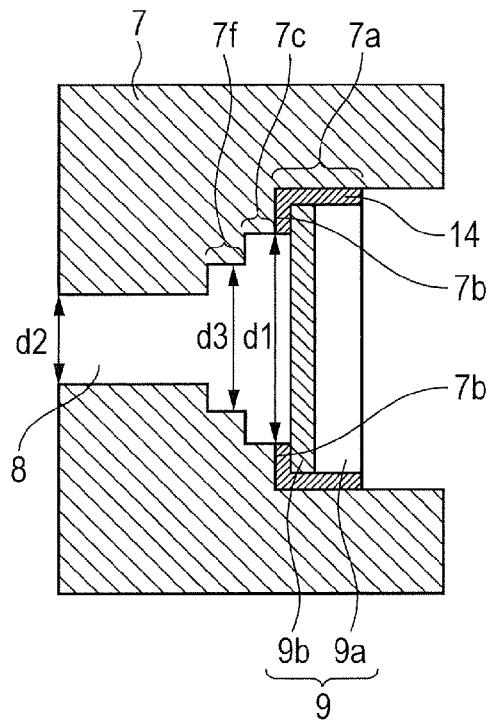

A fourth embodiment will be described with reference to FIG. 2C. FIG. 2C is a cross-sectional view enlargingly illustrating an anode of a radiation generating tube of the present embodiment.

The radiation generating tube of the present embodiment has two step shapes provided from a target supporting surface 7b toward the end in the electron incident side of an electron passing hole 8, in other words, toward an electron incident aperture, which is a point different from that in the first embodiment. Except for this point, the radiation generating tube of the present embodiment employs the same members as those in the first embodiment, and has the same structure as in the first embodiment.

In the structure of FIG. 2C, two step shapes are provided from the target supporting surface 7b toward the end in the electron incident side of the electron passing hole 8, in other words, toward the electron incident aperture so that d1 is larger than d2. The first step shape constitutes a first brazing filler receiving portion 7c, and the second step shape constitutes a second brazing filler receiving portion 7f. When the width of a sectional area in the second brazing filler receiving portion 7f of the electron passing hole 8 is expressed by d3, the relationship among d1, d2 and d3 is expressed by d1>d3>d2. The electron passing hole 8 has a sectional area of which width decreases step by step from the target supporting surface 7b toward the end in the electron incident side of the electron passing hole 8, in other words, toward the electron incident aperture. Because of this, even though the brazing filler has flowed from the target supporting surface 7b and has reached the first step shape and the second step shape, the brazing filler remains in the step shapes, which can prevent the brazing filler from flowing down onto the inner surface of the electron passing hole 8 closer to the electron incident side than the second step shape. Therefore, the structure can prevent the electron beam from directly colliding with the brazing filler.

Thus, with the radiation generating tube according to the present embodiment, an anode 10 configured as shown in FIG. 2C can suppress the lowering of the vacuum degree and the lowering of the radiation quantity originating in the lowering of the vacuum degree, similarly to that in the first embodiment.

The electron passing hole 8 may have a sectional area the width of which discontinuously decreases step by step from the target supporting surface 7b toward the end in the electron incident side of the electron passing hole 8, in other words, toward the electron incident aperture.

Fifth Embodiment

Figure 2D:
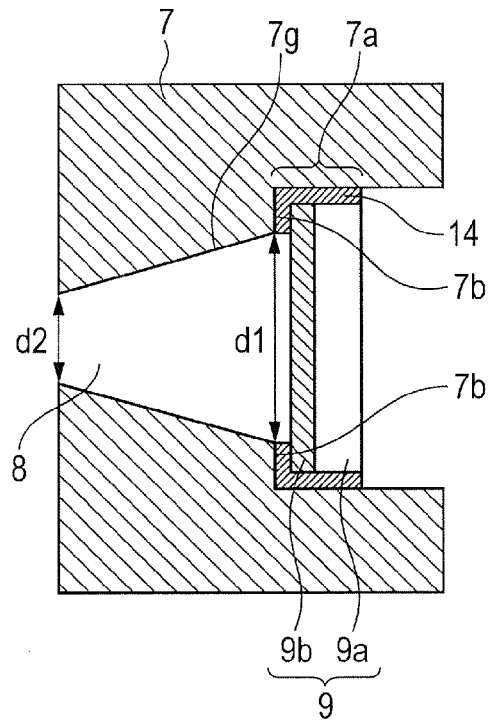

A fifth embodiment will be described reference to FIG. 2D. FIG. 2D is a cross-sectional view enlargingly illustrating an anode of a radiation generating tube of the present embodiment.

The radiation generating tube of the present embodiment has a declining portion 7g provided from a target supporting surface 7b to the end in the electron incident side of an electron passing hole 8, which is a point different from that in the first embodiment. Except for this point, the radiation generating tube of the present embodiment employs the same members as those in the first embodiment, and has the same structure as in the first embodiment.

In the structure of FIG. 2D, the declining portion 7g is provided from the target supporting surface 7b to the end in the electron incident side of the electron passing hole 8, in other words, to the electron incident aperture so that d1 is larger than d2. The declining portion 7g plays a role of the brazing filler receiving portion. The electron passing hole 8 has a sectional area of which width continuously decreases from the target supporting surface 7b to the end in the electron incident side of the electron passing hole 8, in other words, to the electron incident aperture. Because of this, even if the brazing filler has flowed from the target supporting surface 7b and deposited on the inner surface of the electron passing hole 8, the radiation generating tube can prevent the electron beam from directly colliding with the deposited brazing filler.

Thus, with the radiation generating tube according to the present embodiment, the anode 10 configured as shown in FIG. 2D can suppress the lowering of the vacuum degree and the lowering of the radiation quantity originating in the lowering of the vacuum degree, similarly to that in the first embodiment.

Sixth Embodiment

A sixth embodiment of the present invention is a radiation imaging apparatus (not shown) using a radiation generating tube. The radiation imaging apparatus of the present embodiment includes a radiation generating tube, a radiation detector, a signal processing portion, a device control portion and a display portion. The radiation detector is connected to the device control portion through the signal processing portion, and the device control portion is connected to the display portion and a voltage control portion. The radiation generating tube according to the first to fifth embodiments can be used as the radiation generating tube.

The processing in the radiation generating tube is generally controlled by the device control portion. The device control portion controls, for instance, a radiation imaging operation by the radiation generating tube and the radiation detector. The radiation which has been emitted from the radiation generating tube is detected by the radiation detector through a subject, and a radiation transmission image of the subject is taken. The taken radiation transmission image is displayed on the display portion. The device control portion also controls, for instance, the driving of the radiation generating tube, and controls a voltage signal applied to a radiation emitting source, through the voltage control portion.

Thus, the radiation imaging apparatus according to the present embodiment can suppress the lowering of the vacuum degree and the lowering of the radiation quantity originating in the lowering of the vacuum degree, similarly to that in the first to fifth embodiments.

Exemplary Embodiment

An exemplary embodiment of the present invention will be described below with reference to FIGS. 1A to 1C. In the present exemplary embodiment, a radiation emitting source illustrated in FIGS. 1A to 1C was produced. The production method will be described below.

A high-pressure synthesis diamond was prepared as a target substrate 9a. A high-pressure and high-temperature diamond has a disk shape (columnar shape) with a diameter of 5 mm and a thickness of 1 mm. An organic matter existing on the surface of the diamond was removed beforehand with a UV-ozone asher.

A titanium layer was formed beforehand on one surface with a diameter of 1 mm of this diamond substrate with a sputtering method which used Ar as a carrier gas, and then a tungsten layer with a thickness of 8 μm was formed as a target film 9b. Thus, a target 9 was obtained.

A metallization layer which used titanium as an active metal component was formed in the perimeter of this target 9, and a brazing filler formed of silver, copper and titanium was applied on to the metallization layer.

On the other hand, tungsten was prepared as a radiation shielding member 7, and a target supporting portion 7a, a target supporting surface 7b, a brazing filler receiving portion 7c and an electron passing hole 8 were formed, as illustrated in FIG. 1B. The diameter of the target supporting portion 7a was set at 5.3 mm, and the width d1 of a sectional area in the opening in the opposite side of the end in the electron incident side of the electron passing hole 8 was set at 3.5 mm The height of the brazing filler receiving portion 7c was set at 2.0 mm, and the width d2 of the sectional area in the end in the electron incident side of the electron passing hole 8, in other words, the opening size d2 of the electron incident aperture was set at 2.0 mm.

The target 9 on which the brazing filler was provided was set in the radiation shielding member 7 which had been worked into the above described shape, and was baked at 850° C. Thus, the anode 10 was produced.

Next, the anode 10 formed by integrating the target 9 with the radiation shielding member 7 was positioned so that an impregnation type thermoelectron gun having an electron emitting portion 2 opposed to the electron emitting source 3 and so that an electron beam 5 was incident on the electron passing hole 8, as illustrated in FIGS. 1A to 1C, and was vacuum-sealed. Thus, a radiation emitting source 1 was produced. A getter 12 as well was arranged in a vacuum chamber 6. At this time, in order to monitor the vacuum degree in the inside, a pressure gauge was also provided.

Thus, five pieces of radiation emitting sources were produced, and were used as radiation emitting sources of Exemplary Embodiments Nos. 1 to 5, respectively.

Comparative Example

A target 9 similar to that of the above described exemplary embodiment was produced by using a radiation shielding member 7 illustrated in FIG. 3, as a comparative example. After that, an anode 10 was produced in a similar way to that in the above described exemplary embodiment, and furthermore, a radiation emitting source for the comparative example was produced in the similar way. In addition, a pressure gauge was also provided similarly in order to monitor the vacuum degree in the inside. Five pieces of radiation emitting sources were produced also for this comparative example, and were used as radiation emitting sources of Comparative Examples Nos. 1 to 5, respectively.

<Measurement Of Vacuum Degree And Radiation Quantity>

The internal pressures of both of the radiation emitting source in the exemplary embodiment and the radiation emitting source in the comparative example were monitored, and while the internal pressures were monitored, simultaneously the radiation quantities were measured with a semiconductor type of dose meter. The radiation emitting source was driven with an accelerating voltage of 100 kV and an electric current of 5 mA, for an irradiation period of time of 10 msec and a stopping period of time of 90 msec. The diameter of the electron beam was determined to be 1.7 mm from the size of a focal diameter which was separately measured.

Table 1 illustrates changes of pressures and radiation quantities of each of the radiation emitting sources of Exemplary Embodiments Nos. 1 to 5 and each of the radiation emitting sources of Comparative Examples Nos. 1 to 5.

In Exemplary Embodiments No. 2, No. 4 and No. 5, the internal pressures slightly increase. The internal pressures of Exemplary Embodiments No. 1 and No. 3 largely increase compared to those of Exemplary Embodiments No. 2, No. 4 and No. 5. In all of Exemplary Embodiments Nos. 1 to 5, the radiation quantities were the same as those in the beginning, and the lowering of the radiation quantities according to the number of pulse generation times was not observed.

On the other hand, in Comparative Examples No. 2 and No. 4, the internal pressures slightly increase. The internal pressures of Comparative Examples No. 1, No. 3 and No. 5 largely increase. In Comparative Examples No. 2 and No. 4, the lowering of the radiation quantities according to the number of pulse generation times was not observed, but in Comparative Examples No. 1, No. 3 and No. 5, the radiation quantities decreased as the number of the pulse generation times increased.

From the above described result, it is assumed that the used brazing filler did not flow to the inner surface of the electron passing hole 8 of the radiation shielding member 7, in Exemplary Embodiments No. 2, No. 4 and No. 5 and Comparative Examples No. 2 and No. 4. On the other hand, it is assumed that the brazing filler flowed out, in Exemplary Embodiments No. 1 and No. 3 and Comparative Examples No. 1, No. 3 and No. 5. It is assumed that the electron beam directly collided with the brazing filler, accordingly the internal pressure increased, and the amount of generated thermoelectrons decreased, which caused the lowering of the radiation quantity, in Comparative Examples No. 1, No. 3 and No. 5. In Exemplary Embodiments No. 1 and No. 3, the electron beam did not collide with the brazing filler; accordingly, even though the internal pressure increased, the degree was not so much as to cause the lowering of the radiation quantity; and the effect was shown.

TABLE 1

| | | Number of pulse generation times (time) | | | |
|---|---|---|---|---|---|
| | | 1 | 100 | 500 | 1000 |
| Exemplary embodiment 1 | Internal pressure (Pa) | 1E−5 | 4E−5 | 5E−5 | 5E−5 |
| | Radiation quantity (100 at beginning) | 100 | 100 | 100 | 100 |
| Exemplary embodiment 2 | Internal pressure (Pa) | 1E−5 | 3E−5 | 3E−5 | 3E−5 |
| | Radiation quantity (100 at beginning) | 100 | 100 | 100 | 100 |
| Exemplary embodiment 3 | Internal pressure (Pa) | 1E−5 | 4E−5 | 5E−5 | 5E−5 |
| | Radiation quantity (100 at beginning) | 100 | 100 | 100 | 100 |
| Exemplary embodiment 4 | Internal pressure (Pa) | 1E−5 | 3E−5 | 3E−5 | 3E−5 |
| | Radiation quantity (100 at beginning) | 100 | 100 | 100 | 100 |
| Exemplary embodiment 5 | Internal pressure (Pa) | 1E−5 | 3E−5 | 3E−5 | 3E−5 |
| | Radiation quantity (100 at beginning) | 100 | 100 | 100 | 100 |

TABLE 1-continued

| | | \multicolumn{4}{c}{Number of pulse generation times (time)} | | | |
|---|---|---|---|---|---|
| | | 1 | 100 | 500 | 1000 |
| Comparative Example 1 | Internal pressure (Pa) | 1E−5 | 3E−3 | 5E−3 | 8E−3 |
| | Radiation quantity (100 at beginning) | 100 | 90 | 80 | 60 |
| Comparative Example 2 | Internal pressure (Pa) | 1E−5 | 3E−5 | 3E−5 | 3E−5 |
| | Radiation quantity (100 at beginning) | 100 | 100 | 100 | 100 |
| Comparative Example 3 | Internal pressure (Pa) | 1E−5 | 3E−3 | 4E−3 | 8E−3 |
| | Radiation quantity (100 at beginning) | 100 | 95 | 85 | 70 |
| Comparative Example 4 | Internal pressure (Pa) | 1E−5 | 3E−5 | 3E−5 | 3E−5 |
| | Radiation quantity (100 at beginning) | 100 | 100 | 100 | 100 |
| Comparative Example 5 | Internal pressure (Pa) | 1E−5 | 3E−3 | 5E−3 | 8E−3 |
| | Radiation quantity (100 at beginning) | 100 | 95 | 85 | 70 |

Radiation generating tube

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2011-189108, filed Aug. 31, 2011, which is hereby incorporated by reference herein in its entirety.

The invention claimed is:

1. A radiation generating tube comprising:
a cathode having an electron emitting source;
an anode having a target spaced from said electron emitting source, for generating radiation responsive to an irradiation with an electron emitted from the electron source; and
a tubular shielding member having an electron passing hole which has an electron incident aperture at one end thereof and has a target supporting surface supporting said target at the other end thereof,
wherein said target supporting surface is connected through a brazing filler to a periphery of a surface of said target at a side on which the electron is incident, and
wherein said anode has an annular recess located between said target supporting surface and said electron passing hole in said tubular shielding member.

2. The radiation generating tube according to claim 1, wherein said annular recess has, in a cross-section, a rectangular shape or inclined slope shape.

3. The radiation generating tube according to claim 2, wherein said annular recess is shaped to extend a distance along a surface of said shielding member from said target supporting surface to an inner surface of said electron passing hole.

4. The radiation generating tube according to claim 1, wherein said target contains a target metal of atomic number 24 or more.

5. The radiation generating tube according to claim 4, wherein said target metal includes any one of: tungsten, molybdenum, chromium, copper, cobalt, iron, and rhodium, or any alloy thereof.

6. The radiation generating tube according to claim 1, wherein said target is provided with a transmitting substrate containing, as a main ingredient, diamond, silicon nitride, or aluminum nitride.

7. The radiation generating tube according to claim 6, wherein said transmitting substrate is a diamond substrate containing diamond as a main ingredient.

8. The radiation generating tube according to claim 6, wherein said target metal forms a target layer on said transmitting substrate, and said target layer is arranged on a side of said target facing said electron emitting source.

9. The radiation generating tube according to claim 6, wherein said target supporting surface supports at least said transmitting substrate.

10. The radiation generating tube according to claim 8, wherein said transmitting substrate has a coated surface on which said target layer is arranged, and wherein said transmitting substrate has a thickness in a direction normal to said coated surface in a range from 0.3 mm to 2 mm.

11. The radiation generating tube according to claim 8, wherein said target layer has a thickness in a normal direction thereof in a range from 1 µm to 15 µm.

12. The radiation generating tube according to claim 1, wherein said brazing filler is a Cr—V series brazing material, a Ti—Ta—Mo series brazing material, a Ti—V—Cr—Al series brazing material, a Ti—Cr series brazing material, a Ti—Zr—Be series brazing material, a Zr—Nb—Be series brazing material, an Au—Cu series brazing material, a nickel series brazing material, a brass series brazing material, a silver brazing material, or a palladium brazing material.

13. The radiation generating tube according to claim 1, wherein said tubular shielding member has a backward shielding portion for shielding at least a part of the radiation emitted from said target toward said electron source.

14. The radiation generating tube according to claim 1, wherein said tubular shielding member extends toward a surface of said target opposite to a surface of said target irradiated with the electron, and has a forward shielding portion for shielding at least a part of the radiation emitted from said target.

15. A radiation generating apparatus comprising:
the radiation generating tube according to claim 1;
a power source for driving said radiation generating tube; and
a container holding said radiation generating tube.

16. A radiation imaging apparatus comprising:
a radiation generating apparatus according to claim 15; and
a radiation detector for detecting the radiation emitted from said radiation generating apparatus and transmitted through an object.

17. The radiation generating tube according to claim 1, wherein said annular recess surrounds said electron passing hole in said anode.

18. The radiation generating tube according to claim 1, wherein said supporting surface, said annular recess and said electron passing hole are aligned in this order along a radial direction of said target such that brazing filler is prevented from flowing from said supporting surface to said electron passing hole.

19. An X-ray generating tube comprising:
a cathode including an electron emitting source emitting an electron; and an anode including
- a target generating an X-ray upon being irradiation by an electron emitted from said electron emitting source, and
- a tubular shielding member having an annular secured portion, and having a tubular inner wall defining an electron passing hole, wherein said target is secured to said annular secured portion via a bonding member annularly, and wherein said anode has an annular recess located between said annular secured portion and said tubular inner wall in said tubular shielding member.

20. The X-ray generating tube according to claim 19, wherein said annular recess surrounds said electron passing hole.

21. The X-ray generating tube according to claim 19, wherein said annular secured portion, said annular recess and said tubular inner wall are aligned in that order along a radial direction of said target such that said bonding member is prevented from flowing from said secured portion to said tubular inner wall.

22. The X-ray generating tube according to claim 19, wherein said annular secured portion, said annular recess and said tubular inner wall are aligned in this order along a radial direction of said target such that said annular recess prevents the electron beam from directly colliding with any of said bonding member which has flowed out from said secured portion.

* * * * *